(12) United States Patent
Osbon et al.

(10) Patent No.: US 8,137,262 B2
(45) Date of Patent: *Mar. 20, 2012

(54) KIT, SYSTEM AND METHOD TO TREAT ERECTILE DYSFUNCTION

(75) Inventors: Julian Osbon, Augusta, GA (US); John Magee, North Augusta, SC (US)

(73) Assignee: Augusta Medical Systems, Inc., Augusta, GA (US)

( * ) Notice: Subject to any disclaimer, the term of this patent is extended or adjusted under 35 U.S.C. 154(b) by 1344 days.

This patent is subject to a terminal disclaimer.

(21) Appl. No.: 11/581,608

(22) Filed: Oct. 16, 2006

(65) Prior Publication Data

US 2007/0129600 A1 Jun. 7, 2007

Related U.S. Application Data

(63) Continuation-in-part of application No. 11/391,102, filed on Mar. 28, 2006, now Pat. No. 7,186,213, which is a continuation of application No. 10/271,821, filed on Oct. 16, 2002, now Pat. No. 7,037,256.

(51) Int. Cl.
*A61F 5/00* (2006.01)

(52) U.S. Cl. ......................................................... 600/38

(58) Field of Classification Search .............. 600/38–41; 128/844, 897, 898
See application file for complete search history.

(56) References Cited

U.S. PATENT DOCUMENTS

| | | | |
|---|---|---|---|
| 4,856,498 A | 8/1989 | Osbon | |
| 5,094,230 A | 3/1992 | Clark, Jr. | |
| 5,306,227 A * | 4/1994 | Osbon et al. | 600/41 |
| 5,344,389 A * | 9/1994 | Walsdorf et al. | 600/41 |
| 5,624,378 A | 4/1997 | Baldecchi | |
| 5,695,444 A * | 12/1997 | Chaney | 600/38 |
| 6,183,414 B1 | 2/2001 | Wysor et al. | |
| 6,306,080 B1 | 10/2001 | Mitchell et al. | |
| 6,926,666 B2 * | 8/2005 | Magee | 600/38 |
| 7,037,256 B2 * | 5/2006 | Osbon et al. | 600/38 |
| 7,186,213 B2 * | 3/2007 | Osbon et al. | 600/38 |

OTHER PUBLICATIONS

J. Paul Yurkanin, Effect of Incision and Saphenous Vein Grafting for Peyronie's Disease on Penile Length and Sexual Satisfaction, The Journal of Urology, vol. 166, 1769-1773, (Nov. 2001).

Lawrence S. Hakim, Vacuum Erection Associated Impotence and Peyronie's Disease, The Journal Of Urology, vol. 155, 534-535 (Feb. 1996).

(Continued)

*Primary Examiner* — Samuel Gilbert
(74) *Attorney, Agent, or Firm* — Bracewell and Giuliani LLP

(57) ABSTRACT

Embodiments of the present invention advantageously provide kits, systems, and methods for treating a patient's erectile dysfunction. An embodiment of a kit, for example, includes a pressure pump, a plurality of elongated vacuum chambers, and a plurality of penile tension devices positioned in a container. An embodiment of a system, for example, includes a pressure pump, an elongated vacuum chamber selected from a plurality of elongated vacuum chambers positioned in a kit, and a penile tension device selected from a plurality of penile tension devices positioned in a kit. An embodiment of a method, for example, includes examining a patient, selecting an elongated vacuum chamber from a plurality of vacuum chambers positioned in a kit based upon the examination, and selecting a penile tension device from a plurality of penile tension devices positioned in the kit responsive to the examination.

31 Claims, 12 Drawing Sheets

OTHER PUBLICATIONS

Tom F. Lue, Lengthening Shortened Penis Caused by Peyronie's Disease Using Circular Venous Grafting and Daily Stretching With a Vacuum Erection Device, The Journal of Urology, vol. 161, 1141-1144, (Apr. 1999).

Tension Bands and Accessories; online sales brochure; downloaded from www.erecaidpumps.com/erecaidbands.htm on Apr. 4, 2011; 5 pages.

Osbon.com; website; downloaded from www.osbon.com.au/tension_rings.php on Apr. 4, 2011; 1 page.

ErecAid Tension Bands by Timm Osbon; online sales brochure; downloaded from www.vitalitymedical.com on Apr. 4, 2011; 2 pages.

What Size Tension Band Should I Get?; online sales brochure; downloaded from www.vitalitymedical.com on Apr. 4, 2011; 1 page.

* cited by examiner

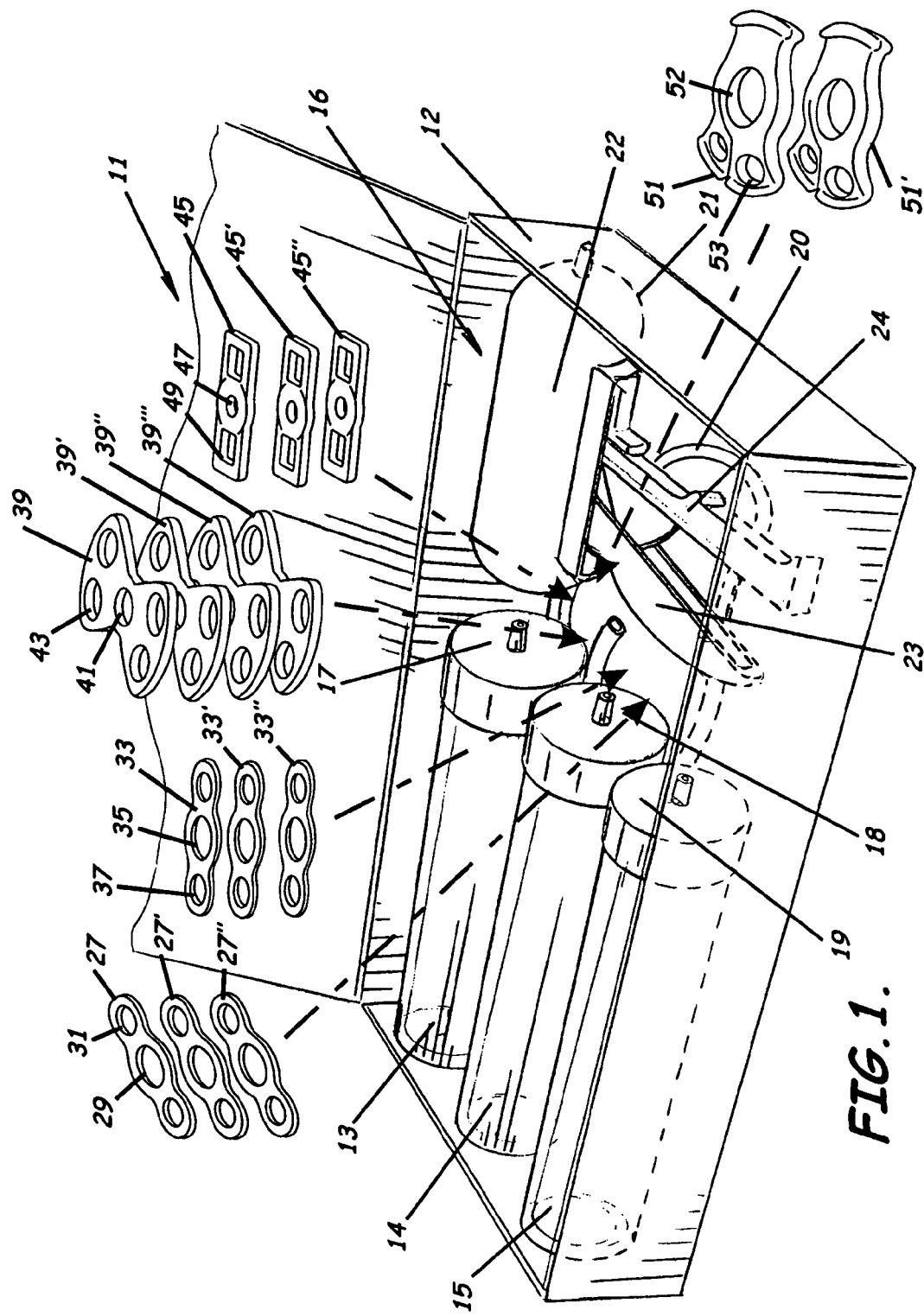

| Image | Tension System Name | Material | Tension Type | Center Opening Inches | Center Opening Millimeters |
|---|---|---|---|---|---|
| | Select #4 | C-Flex® | Standard | 5/8" | 16.51 |
| | Select #5 | C-Flex® | Standard | 3/4" | 19.05 |
| | Select #6 | C-Flex® | Standard | 7/8" | 22.22 |
| | Ultra #4 | Kraton® | Strong | 5/8" | 16.51 |
| | Ultra #5 | Kraton® | Strong | 3/4" | 19.05 |
| | Ultra #6 | Kraton® | Strong | 7/8" | 22.22 |
| | SureEase Comfort #1 | DynaFlex® | Light | 3/8" | 9.52 |
| | SureEase Comfort #2 | Dynaflex® | Light | 1/2" | 12.70 |
| | SureEase Ultra #3 | Dynaflex® | Standard | 5/8" | 16.51 |
| | SureEase Ultra #4 | Dynaflex® | Standard | 3/4" | 19.05 |
| | Ultimate #0 | Dynaflex® | Light | 3/8" | 9.05 |
| | Ultimate #1 | Dynaflex® | Light | 7/16" | 11.09 |
| | Ultimate #2 | Dynaflex® | Light | 1/2" | 12.70 |
| | SureRelease Enhanced | Dynaflex® | Standard | 1/2" | 12.70 |
| | SureRelease Standard | Dynaflex® | Standard | 3/4" | 19.05 |

FIG. 2.

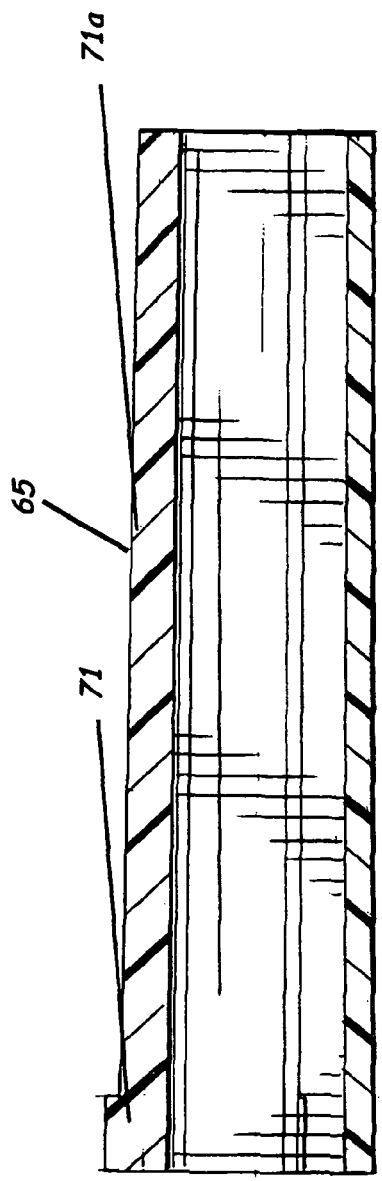
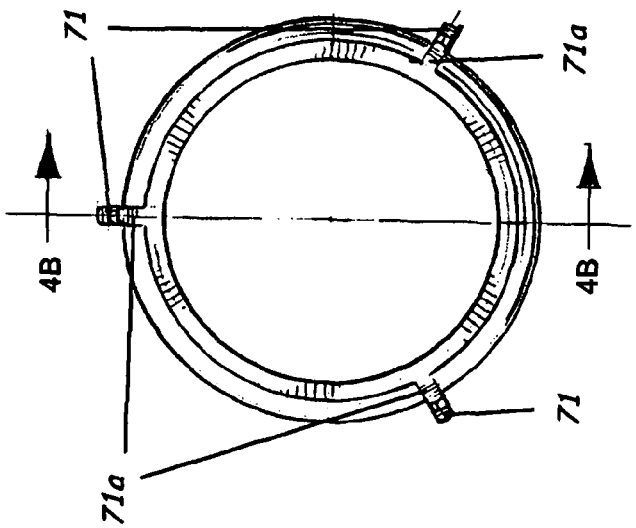
FIG. 4B.
FIG. 4A.

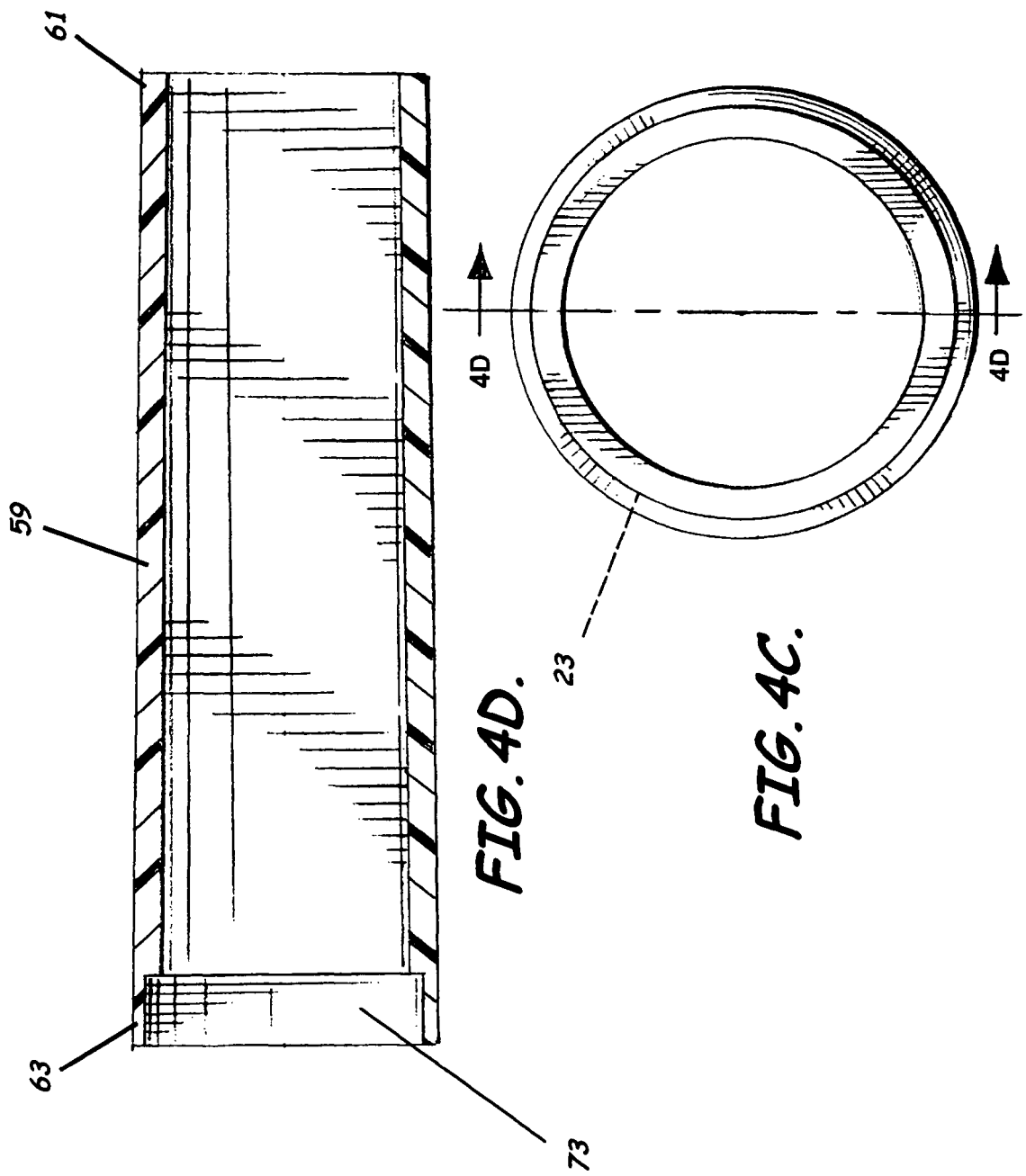

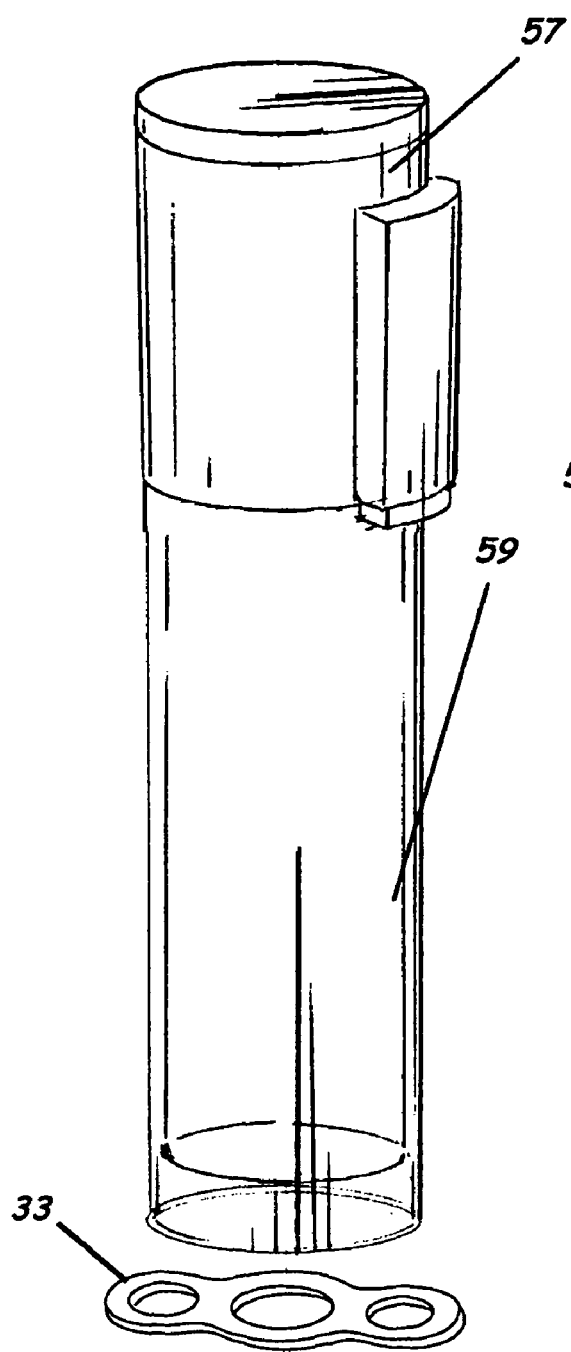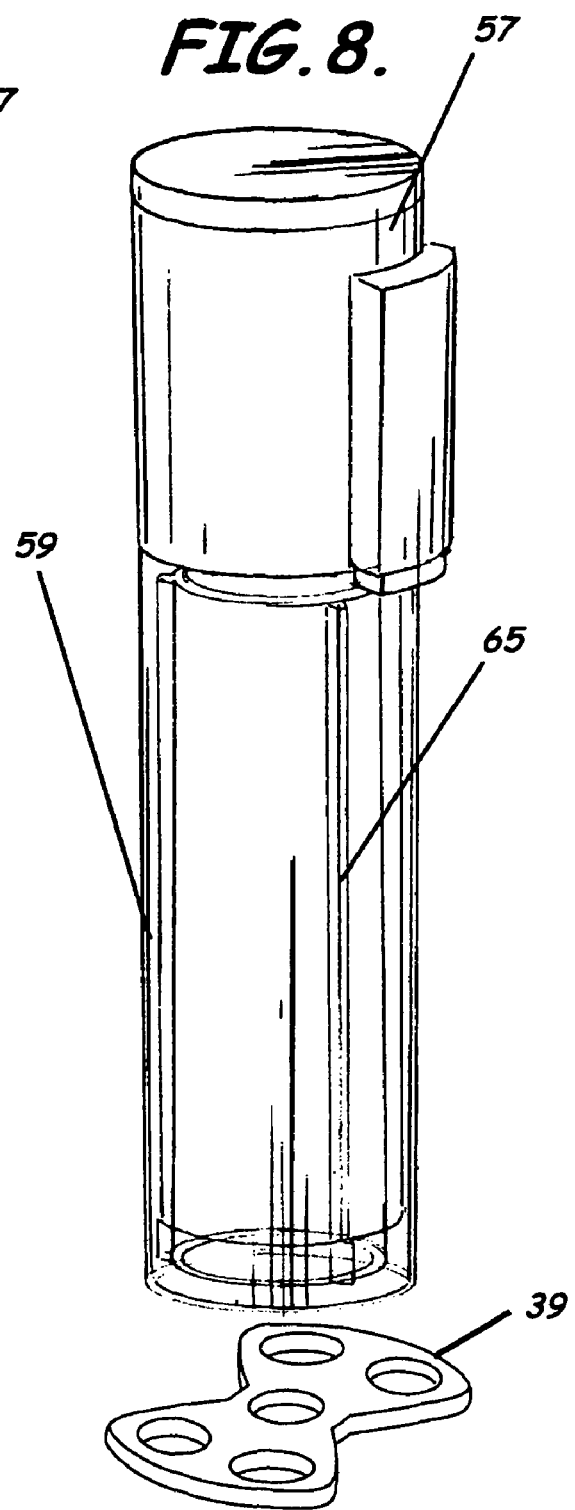

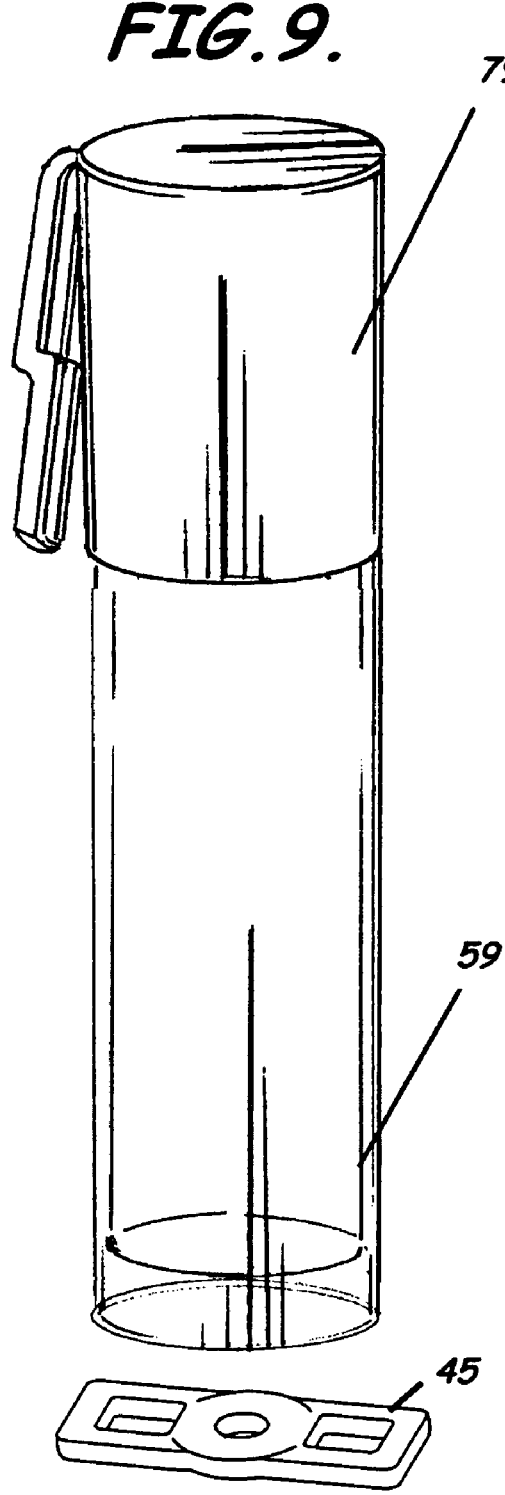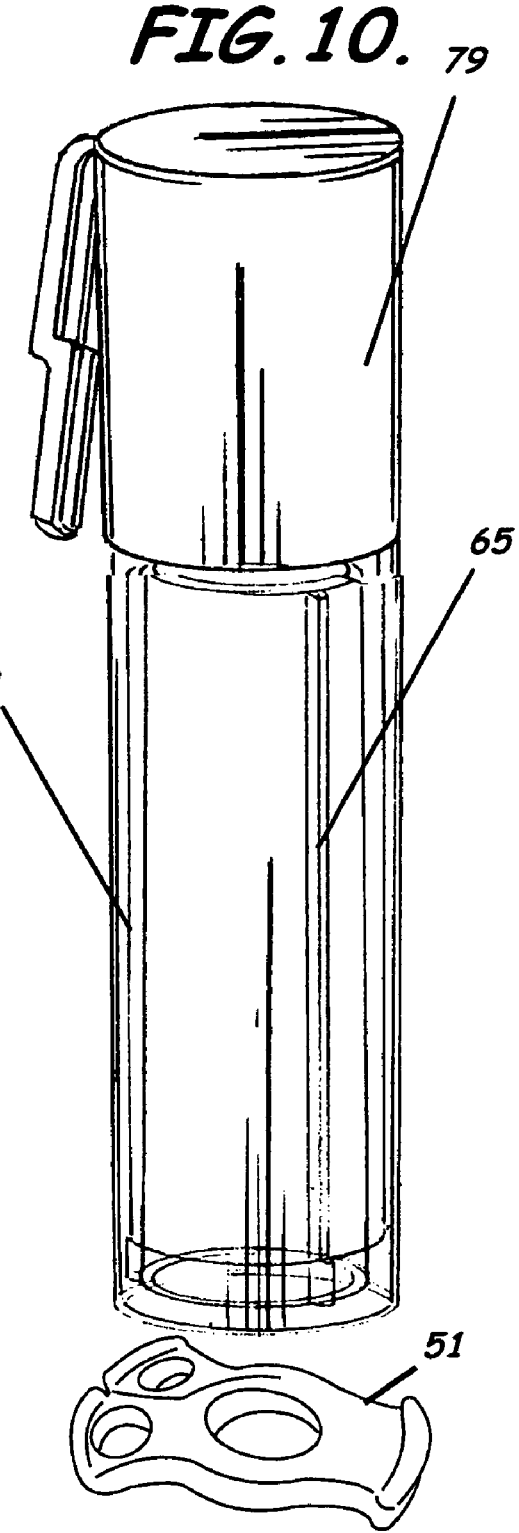

KIT, SYSTEM AND METHOD TO TREAT ERECTILE DYSFUNCTION

RELATED APPLICATION

This application is a continuation-in-part of and claims benefit and priority to U.S. patent application Ser. No. 11/391,102, filed on Mar. 28, 2006, which is a continuation of U.S. patent application Ser. No. 10/271,821, filed Oct. 16, 2002, now issued U.S. Pat. No. 7,037,256, both of which are incorporated herein by reference in their entireties.

FIELD OF THE INVENTION

The present invention relates to the field of medical treatment and, more particularly, to erectile dysfunction kits, systems, and methods.

BACKGROUND OF THE INVENTION

The male penis includes a pair of corpora cavernosa located laterally within the penis, a pair of penile arteries situated deep within their respective corpora cavernosa, dorsal penal veins and a neurovascular bundle located along an upper portion of the penis, a corpus spongiosum located along a lower portion of the penis, a urethra located within the corpus spongiosum, and stretchable skin surrounding thereabout. Generally, in the male penis, an erection is produced when arterial blood flows to the erectile tissues of the penis with the veinal return flow of blood to the body restricted so that the erectile tissues become filled or engorged with blood. The restriction is normally performed by sphincter muscles which function in response to sexual arousal. Some men have various problems, e.g., advancing age, physiological or psychological problems, or premature relaxation prior to completion of coitus. This often leaves these men unsatisfied with the sex act process.

Vacuum erection therapy is recognized as a potential remedy, preferable to many other treatments of erection dysfunction such as injections, venous and arterial surgery, or implantation of a penile prosthesis. It provides a firm erection in the shortest time, without need of sexual arousal and can be faster than pills. Vacuum treatment devices include a vacuum chamber with an open end serving as a passage for the penis and a closed end connected to a vacuum pump. To achieve an erection the penis is inserted into the open end of the vacuum chamber, which is pressed to the abdomen to form an airtight seal. A vacuum is then generated in the chamber with the manually or electrically operated pump. The vacuum inside the chamber causes blood flow into the penis which thereby produces an erection. The vacuum, however, must be removed for coitus, and thus, the erection can be lost.

By the recognition that penile arteries are located primarily in the deep interior of the male penis, and the return veins are located in a sub-dermal region along the surface of the organ, it has been known to secure a band of material around the base of the penis closely adjacent a user's body to restrict the return veinal blood flow. This assists in maintaining an erection while the arterial flow remains substantially unimpeded, i.e., the arteries are deep within the organ and protected from pressure by the erectile tissue.

Over the years, various vacuum treatment devices for treating a patient's male sexual organ have been developed. Various types and configurations of penile tension devices for assisting in the restriction of the return veinal blood flow also have been developed. Although the size and shape of patients' penises vary greatly, proper sizing of vacuum chambers and penile tension devices has remained a difficult process for patients.

SUMMARY OF THE INVENTION

It has been observed that patients often must make due with a vacuum chamber or penile tension device that is not sized to their particular anatomy or selected to treat their particular severity of erectile dysfunction. The typical patient purchases only one vacuum chamber and a limited selection of penile tension devices. The patient is then left to experiment with the few items he has purchased on his own and without the knowledge and assistance of a professional. Patients thus often do not use a vacuum treatment system having the correct size vacuum chamber or penile tension device, or suffer the aggravation and cost of purchasing multiple vacuum treatment systems before discovering the correct system for the patient's particular needs. Furthermore, the proper vacuum chamber and penile tension device for a particular patient can change as the level of engorgement of the patient's penis and severity of erectile dysfunction changes during treatment. Thus, a vacuum treatment system that initialed meets the needs of a particular patient can fail to meet those needs in the future.

Patients using the wrong size vacuum chamber or penile tension device may not receive the comfort and performance they otherwise could receive. A vacuum chamber that is too large can make an air-tight seal between the vacuum chamber and abdomen of the patient more difficult to attain. Furthermore, an overly large vacuum chamber can require more time and effort to evacuate before a negative pressure is created therein. A vacuum chamber that is too small can create patient discomfort and can prevent the penis from receiving the level of treatment it otherwise would receive. A penile tension device that is too large or provides too little tension cannot adequately restrict veinal blood flow. A penile tension device that is too small or provides too much tension can create patient discomfort; is more difficult to remove, place, and reposition; and, if left in the constricted position, can cause pain and bruising to the penis.

With the forgoing in mind, embodiments of the present invention advantageously provide a kit and a system having a plurality of sizing options for treating a patient's erectile dysfunction. Also, embodiments of the present invention advantageously provide a method of treating erectile dysfunction wherein the vacuum chamber and penile tension device of a vacuum treatment system are properly selected for a patient.

More specifically, an embodiment of the present invention advantageously provides a kit for treating a patient's erectile dysfunction. This kit preferably includes a pressure pump, a plurality of elongated vacuum chambers, and a plurality of penile tension devices positioned in a container. Each of the plurality of vacuum chambers preferably has a proximal and distal longitudinal ends. The proximal longitudinal end of each of the vacuum chambers is adapted to receive a patient's penis while a distal longitudinal end of the vacuum chambers is adapted to be positioned in fluid communication with the pressure pump. When the pressure pump is operating, a pressure is created inside the selected vacuum chamber and exerted upon the penis received therein. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. A first one of the plurality of penile tension devices preferably differs from a second one of the plurality of penile tension devices. For example, the kit most preferably includes an assortment of penile tension devices differing in inner circumference, material composition, tension type, and grip design so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices.

An embodiment of the present invention also advantageously provides a system for treating erectile dysfunction. This system preferably includes a pressure pump, an elongated vacuum chamber selected from a plurality of elongated vacuum chambers positioned in a kit, and a penile tension device selected from a plurality of penile tension devices positioned in a kit. The vacuum chamber is positioned in fluid communication with the pressure pump at a distal longitudinal end thereof. A proximal longitudinal end of the vacuum chamber is adapted to receive a patient's penis. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. A first one of the plurality of penile tension devices preferably differs from a second one of the plurality of penile tension devices. The kit most preferably includes an assortment of penile tension devices differing in inner circumference, material composition, tension type, and grip design so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices.

Additionally, the present invention advantageously includes methods of treating erectile dysfunction. An embodiment of a method, for example, preferably includes examining a patient in order to determine at least the length and girth of the patient's penis and the severity of the patient's erectile dysfunction, selecting an elongated vacuum chamber from a plurality of vacuum chambers positioned in a kit based upon the examination, and selecting a penile tension device from a plurality of penile tension devices positioned in the kit based upon the examination. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. A first one of the plurality of penile tension devices preferably differs from a second one of the plurality of penile tension devices. The kit most preferably includes an assortment of penile tension devices differing in inner circumference, material composition, tension type, and grip design so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices.

One embodiment of a method may further include placing the patient's penis inside the selected vacuum chamber, pumping air out of the chamber to create a pressure therewithin, maintaining the pressure within the chamber until an erection of a desired magnitude is achieved, removing the vacuum chamber, and stretching the selected penile tension device over a distal end of the patient's penis and toward a proximal portion of the penis.

Another embodiment of a method may further include stretching the selected penile tension device over the proximal longitudinal end of the selected vacuum chamber, placing the patient's penis inside the selected vacuum chamber, pumping air out of the chamber to create a pressure therewithin, maintaining the pressure within the chamber until an erection of a desired magnitude is achieved, repositioning the selected penile tension device off the proximal longitudinal end of the chamber and onto a proximal portion of the penis of the user, and removing the chamber.

Additionally, kits, systems, and methods as may be included by distributing and sizing through an interactive Internet website or other electronic communication as understood by those skilled in the art. For example, a potential user can visit a preselected website to view and study information about a kit or system. The potential user can then follow preselected steps or instructions as to how sizing of a vacuum chamber or penile tensioning device is determined for the particular user, thereby allowing the user more private in home, or other locale, selection. Based on this information, the user can either be directed to a physician for confirmation of sizing and comfort, order a kit having the plurality of sizes of penile tension devices, order a kit having a plurality of vacuum chambers, order one or more preselected vacuum chamber and one or more penile tensioning devices, or one or more combinations as described.

BRIEF DESCRIPTION OF THE DRAWING

Some of the features, advantages, and benefits of the present invention having been stated, others will become apparent as the description proceeds when taken in conjunction with the accompanying drawings in which:

FIG. 1 is an exploded perspective view of a kit to treat erectile dysfunction according to an embodiment of the present invention;

FIG. 2 is a chart illustrating a plurality of pre-selected characteristics of an assortment of penile tension devices shown in FIG. 1 according to an embodiment of the present invention;

FIG. 4A is a front elevational view of an inner vacuum chamber shown in FIG. 3 according to an embodiment of the present invention;

FIG. 4B is a sectional view taken along line 4B-4B of FIG. 4A according to an embodiment of the present invention;

FIG. 4C is a front elevational view of an outer vacuum chamber shown in FIG. 3 according to an embodiment of the present invention;

FIG. 4D is a sectional view taken along line 4D-4D of FIG. 4C according to an embodiment of the present invention;

FIG. 7 is a perspective view of a system to treat erectile dysfunction according to another embodiment of the present invention;

FIG. 8 is a perspective view of a system to treat erectile dysfunction according to another embodiment of the present invention;

FIG. 9 is a perspective view of a system to treat erectile dysfunction according to another embodiment of the present invention;

FIG. 10 is a perspective view of a system to treat erectile dysfunction according to another embodiment of the present invention;

DETAILED DESCRIPTION

Figure 3:
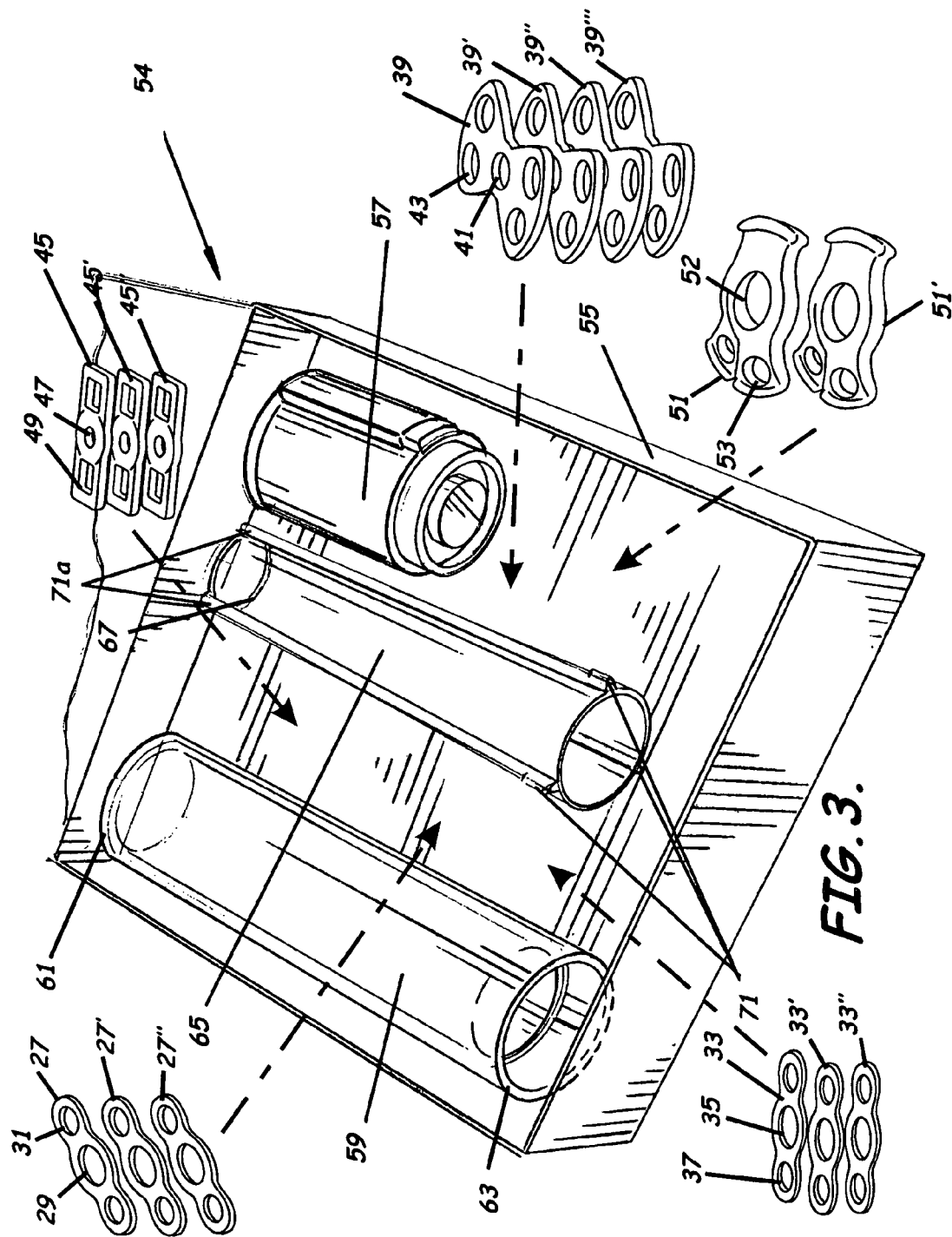
FIG. 3 is an exploded perspective view of a kit to treat erectile dysfunction according to another embodiment of the present invention.

The present invention will now be described more fully hereinafter with reference to the accompanying drawings which illustrate various embodiments of the invention. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime or double prime notation, if used, indicate similar elements in alternative embodiments.

As illustrated in FIGS. 1-5, a kit to treat erectile dysfunction is advantageously placed in a container. This embodiment of a kit preferably includes a pressure pump, a plurality of elongated vacuum chambers, and a plurality of penile tension devices. Each of the at least two elongated vacuum chambers preferably has a proximal and distal longitudinal ends. The proximal end refers to the end brought into contact with a user during operation while an opposite or distal end is generally away from the body (i.e., torso) of the user. The proximal longitudinal end of each of the vacuum chambers is adapted to receive a patient's penis while a distal longitudinal end of the vacuum chambers is adapted to be positioned in fluid communication with a pressure pump as understood by those skilled in the art. When the pressure pump is operating, a pressure is created inside the chamber and exerted upon the extremity received therein. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. These needs can and often change over time or over use of other vacuum chambers. A first one of the plurality of penile tension devices preferably differs from a second one of the plurality of penile tension devices. An embodiment of a kit most preferably includes an assortment of penile tension devices differing in inner circumference, material composition, tension type, and grip design so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices.

As specifically illustrated in FIG. 1, for example, a kit 11 for treating erectile dysfunction includes three elongated vacuum chambers 13, 14, 15 and a pressure pump 16 positioned in a container 12. Each of the three vacuum chambers 13, 14, 15 preferably has a different inner circumference than each of the other ones of the three vacuum chambers (referred to as small, medium and large chambers). When each of the three vacuum chambers 13, 14, 15 is used during operation of the pressure pump 16, patients having penises of different size and erectile dysfunction of varying degrees of severity may receive similar comfort and performance by using the vacuum chamber best suited to the patient's needs during operation of the pressure pump. The three vacuum chamber 13, 14, and 15 also accommodate changes in the same patient over time. For example, a patient who has not had an erection in a long time will have less blood pulled into the penis. With vacuum treatment over time, the tissue inside the penis will hold more blood, resulting in more engorgement and a need for a larger vacuum chamber.

The kit 11 further preferably includes fluid communication establishing means 17, 18, 19 adapted to be connected to each of the three vacuum chambers 13, 14, 15, respectively, for establishing fluid communication between each of the three vacuum chambers 13, 14, 15 and the pressure pump 16. The fluid communication establishing means, for example, can include one or more fluid channels and one or more connector arrangements to allow fluid from a pump to travel from the pump into the vacuum chamber as will be understood by those skilled in the art. Further, the kit 11 can include a flexible tube 20, which has a first end adapted to be connected to the fluid communication establishing means 17, 18, 19 separately and a second end adapted to be connected to the pressure pump 16, to thereby operate as a fluid channel extension and allow more flexible positioning and use of the pump.

As further illustrated in FIG. 1, the pressure pump 16 preferably includes a pump housing 21, a pump actuator 22 positioned in the pump 16, a handle 23 connected to the housing 21, and a pump actuation arm 24 connected to the housing 21 and to the pump actuator 22. When pulling the actuation arm 24 toward the handle 23, one actuates the pressure pump 16. Once the pressure pump 16 is actuated, air is drawn out of the vacuum chambers 13, 14, 15, causing negative pressure (i.e., vacuum) to be created inside the chambers. This negative pressure causes blood to be drawn into the vascular system of the patient's penis creating pressure to cause the penis to become erect.

The pressure pump 16 further advantageously has a built-in pressure limiter. This limiter restricts the amount of negative pressure that can be drawn to a pre-set limit as understood by those skilled in the art. The limiter is located inside the pump and can be pre-set at the manufacturer. The pressure pump handle 23 has a negative pressure release located adjacent the handle. Pressure is released when the handle 23 is pulled toward a user. The amount of pressure released is related to how much the handle is pulled. The more the handle is pulled, the more pressure is released. In the event of too much pressure being drawn during use, one may release gradual amounts of negative pressure until the desired level is achieved.

The kit 11 further preferably includes an assortment of a plurality, e.g., 15, of penile tension devices 27-51' differing in inner circumference, material composition, tension type, and grip design. The assortment of penile tension devices may of course include more or less than 15 penile tension devices, and those devices may differ from one another by characteristics not described herein or not including some or all of the characteristics listed above, the assortment of penile tension devices of kit 11 serving only as an example. An assortment of penile tension devices is included so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices. The assortment of penile tension devices 27-51' also accommodates changes in the same patient over time. For example, with treatment over time, a patient may require less tension from the penile tension device in order to maintain an erection, or vise versa.

An embodiment of a penile tension device or tension system 27 includes inner circumference or center opening 29 and grip design 31. A penile tension device 27 preferably is a Select #4 penile tension device available from Augusta Medical Systems of Augusta, Ga. It preferably is composed of C-Flex®, provides a standard or intermediate level of tension, and has an inner circumference of ⅝ of one inch. C-Flex® is a thermoplastic elastomer available from Consolidated Polymer Technologies, Inc. of Clearwater, Fla. The C-Flex® used here preferably has a durometer of 35 Shore A, elongation of 827%, tear strength of 116 PLI, and tensile strength of 843 PSI. These properties have been found to provide adequate tension for mild to severe erectile dysfunction. Penile tension device 27' preferably is a Select #5 penile tension device available from Augusta Medical Systems of Augusta, Ga. It preferably is composed of C-Flex®, provides a standard or intermediate level of tension, and has an inner circumference of ¾ of one inch. Penile tension device 27" preferably is a Select #6 penile tension device available from Augusta Medical Systems of Augusta, Ga. It preferably is composed of C-Flex®, provides a standard or intermediate level of tension, and has an inner circumference of ⅞ of one inch.

Penile tension device or tension system 33 includes inner circumference or center opening 35 and grip 37. Penile tension device 33 preferably is an Ultra #4 penile tension device available from Augusta Medical Systems of Augusta, Ga. It preferably is composed of Kraton®, provides a strong or high level of tension, and has an inner circumference of ⅝ of one inch. Kraton® is a thermoplastic elastomer available from Kraton Polymers U.S. LLC of Houston, Tex. The Kraton® used here preferably has a durometer of 35 Shore A, elongation of 1210%, tear strength of 350 PLI, and tensile strength of 1500 PSI. These properties have been found to provide adequate tension for severe erectile dysfunction. Penile tension device 33' preferably is an Ultra #5 penile tension device available from Augusta Medical Systems of Augusta, Ga. It preferably is composed of Kraton®, provides a strong or high level of tension, and has an inner circumference of ¾ of one inch. Penile tension device 33" preferably is an Ultra #6 penile tension device available from Augusta Medical Systems of Augusta, Ga. It preferably is composed of Kraton®, provides a strong or high level of tension, and has an inner circumference of ⅞ of one inch.

Penile tension device or tension system 39 includes inner circumference or center opening 41 and grip 43. Penile tension device 39 preferably is a SureEase Comfort #1 penile tension device available from Augusta Medical Systems of Augusta, Ga. It preferably is composed of Dynaflex®, provides a light or low level of tension, and has an inner circumference of ⅜ of one inch. Dynaflex® is a thermoplastic elastomer available from GLS Corporation of Arlington Heights, Ill. The Dynaflex® used for the SureEase Comfort devices preferably has a durometer of 13 Shore A, elongation of 900%, tear strength of 52 PLI, and tensile strength of 580 PSI. These properties have been found to feel soft while providing adequate tension. Penile tension device 39' preferably is a SureEase Comfort #2 penile tension device available from Augusta Medical Systems of Augusta, Ga. It preferably is composed of Dynaflex®, provides a light or low level of tension, and has an inner circumference of ½ of one inch. Penile tension device 39" preferably is a SureEase Ultra #3 penile tension device available from Augusta Medical Systems of Augusta, Ga. It preferably is composed of Dynaflex®, provides a standard or intermediate level of tension, and has an inner circumference of ⅝ of one inch. The Dynaflex® used for the SureEase Ultra devices preferably has a durometer of 30 Shore A, elongation of 650%, tear strength of 100 PLI, and tensile strength of 260 PSI. These properties have been found to provide adequate tension for mild to severe erectile dysfunction. Penile tension device 39'" preferably is a SureEase Ultra #4 penile tension device available from Augusta Medical Systems of Augusta, Ga. It preferably is composed of Dynaflex®, provides a standard or intermediate level of tension, and has an inner circumference of ¾ of one inch. As described herein, the range of inner circumference is between ¼th of an inch to one inch, and more preferably between ⅜ths of an inch to ⅞ths of an inch. The tension level ranges from a light or low level of tension to a strong or high level of tension as understood by those skilled in the art.

Penile tension device or tension system 45 includes inner circumference or center opening 47 and grip 49. Penile tension device 45 preferably is an Ultimate #0 penile tension device available from Augusta Medical Systems of Augusta, Ga. It preferably is composed of Dynaflex®, provides a light or low level of tension, and has an inner circumference of ⅜ of one inch. The Dynaflex® used for the Ultimate devices preferably has a durometer of 13 Shore A, elongation of 900%, tear strength of 52 PLI, and tensile strength of 580 PSI. These properties have been found to feel soft while providing adequate tension. Penile tension device 45' preferably is an Ultimate #1 penile tension device available from Augusta Medical Systems of Augusta, Ga. It preferably is composed of Dynaflex®, provides a light or low level of tension, and has an inner circumference of 7/16 of one inch. Penile tension device 45" preferably is an Ultimate #2 penile tension device available from Augusta Medical Systems of Augusta, Ga. It preferably is composed of Dynaflex®, provides a light or low level of tension, and has an inner circumference of ½ of one inch.

Penile tension device or tension system 51 includes inner circumference or center opening 52 and grip 53. Penile tension device 51 preferably is a SureRelease Enhanced penile tension device available from Augusta Medical Systems of Augusta, Ga. It preferably is composed of Dynaflex®, provides a standard or intermediate level of tension, and has an inner circumference of ½ of one inch. The Dynaflex® used for the SureRelease devices preferably has a durometer of 30 Shore A, elongation of 650%, tear strength of 100 PLI, and tensile strength of 260 PSI. These properties have been found to provide adequate tension while allowing the material to tear easily. Penile tension device 51' preferably is a SureRelease Standard penile tension device available from Augusta Medical Systems of Augusta, Ga. It preferably is composed of Dynaflex®, provides a standard or intermediate level of tension, and has an inner circumference of ¾ of one inch. As illustrated and described, material composition, size, and type of penile tensioning devices can impact tension levels and patient comfort. By providing a preselected range, a physician and patient can more effectively make selections, recommendations, or prescriptions by the use of one kit.

Kit 11 for treating erectile dysfunction optionally may include additional components. For example, a loading cone for assisting in loading a penile tension device on a proximal longitudinal end of a vacuum chamber, cylinder sizing inserts for enhancing an airtight seal between a proximal longitudinal end of a vacuum chamber and the body of a user, a tube of lubricant, an instructional DVD, and an instruction manual could be included, as well as a chart, if desired, such as shown in FIG. 2. FIG. 2 is a chart summarizing the characteristics of the assortment of penile tension devices 27-51' shown in FIG. 1 and as described above.

Additionally, kits, systems, and methods as may be included by distributing and sizing through an interactive Internet website or other electronic communication as understood by those skilled in the art. For example, a potential user can visit a preselected website to view and study information about a kit or system. The potential user can then follow preselected steps or instructions as to how sizing of a vacuum chamber or penile tensioning device is determined for the particular user, thereby allowing the user more private in home, or other locale, selection. Based on this information, the user can either be directed to a physician for confirmation of sizing and comfort, order a kit having the plurality of sizes of penile tension devices, order a kit having a plurality of vacuum chambers, order one or more preselected vacuum chamber and one or more penile tensioning devices, or one or more combinations as described.

Illustrated in FIG. 3 is another example of a kit to treat erectile dysfunction. This kit 54, for example, preferably includes a pressure pump 57, an outer vacuum chamber 59 and at least one inner vacuum chamber 65 positioned in a container 55. The inner vacuum chamber 65 is adapted to be inserted into the outer vacuum chamber 59. The outer vacuum chamber 59 preferably has a proximal longitudinal end 63 adapted to receive a patient's penis and a distal longitudinal end 61 adapted to be positioned in fluid communication with the pressure pump 57. The inner vacuum chamber 65 preferably has a proximal longitudinal end 69 adapted to receive a patient's penis and a distal longitudinal end 67 adapted to be positioned in fluid communication with the pressure pump 57. Depending on the timing during a course of treatment and condition of the penis, the outer vacuum chamber 59 may be connected to and in fluid communication with the pressure pump 57 without the inner vacuum chamber 65 positioned therein. Since the outer vacuum chamber 59 preferably has a different inner circumference than the inner vacuum chamber 65, patients having penises of different size and erectile dysfunction of varying degrees of severity may receive similar comfort and performance by using the vacuum chamber best suited to the patient's needs during operation of the pressure pump. The outer vacuum chamber 59 and inner vacuum chamber 65 also accommodate changes in the same patient over time. For example, a patient who has not had an erection in a long time will have less blood pulled into the penis. With vacuum treatment over time, the tissue inside the penis will hold more blood, resulting in more engorgement and a need for a vacuum chamber with a larger inner circumference.

The kit 54 further preferably includes an assortment of 15 penile tension devices 27-51' differing in inner circumference, material composition, tension type, and grip design. The assortment of penile tension devices may of course include more or less than 15 penile tension devices, and those devices may differ from one another by characteristics not described herein or not including some or all of the characteristics listed above, the assortment of penile tension devices of kit 54 serving only as an example. An assortment of penile tension devices is included so that different patients having penises of different size and erectile dysfunction of varying degrees of severity may receive similar comfort and performance by using the penile tension device best suited to the patient's needs. The assortment of penile tension devices 27-51' also accommodates changes in the same patient over time. For example, with treatment over time, a patient may require less tension from the penile tension device in order to maintain an erection, or vise versa. The preferred characteristics of penile tension devices 27-51' have been describe in relation to FIG. 1 and are summarized in FIG. 2.

A kit 54 to treat erectile dysfunction optionally may include additional components. For example, a loading cone for assisting in loading a penile tension device on a proximal longitudinal end of a vacuum chamber, cylinder sizing inserts for enhancing an air-tight seal between a proximal longitudinal end of a vacuum chamber and the body of a user, a tube of lubricant, an instructional DVD, and an instruction manual could be included, as well as a chart, if desired, such as shown in FIG. 2.

FIGS. 4A, 4B, 4C and 4D illustrate a user interface positioned between the outer surface of the inner vacuum chamber 65 and the inner surface of the outer vacuum chamber 59 shown in FIG. 3. The outer vacuum chamber 59 preferably has an inner flange 73, which is positioned adjacent the proximal longitudinal end 63 of the outer chamber 59 and connected to and extending inwardly from an inner surface of the outer chamber 59. Thereby, an inner step is defined and formed therein from the proximal longitudinal end 63 of the outer chamber 59. The inner vacuum chamber 65 preferably has a plurality of stop members 71 extending outwardly from an outer surface of the inner vacuum chamber 65 to interface with and contact the inner step 73 of the outer vacuum chamber 59 to thereby limit the inward movement of the inner vacuum chamber 65 when positioned within the outer vacuum chamber 59. Further preferably, the inner vacuum chamber 65 has a plurality of spaced-apart ribs 71a connected to and extending outwardly from the outer surface, which provides separation between the outer surface of the inner vacuum chamber 65 and the inner surface of the outer vacuum chamber 59. Therefore, an interstitial space is formed between the two surfaces when the inner vacuum chamber 65 is positioned within the outer vacuum chamber 59.

Figure 5:
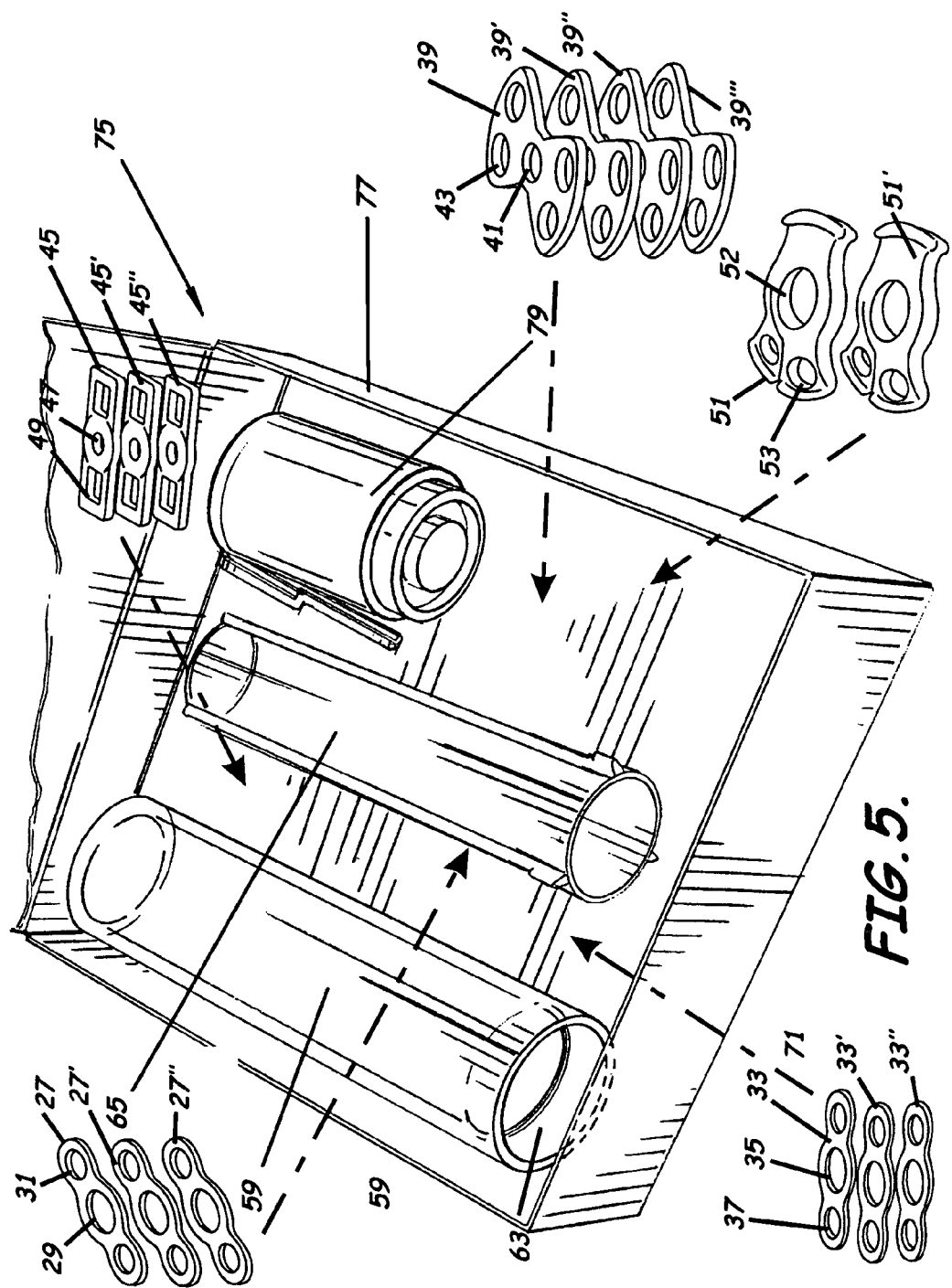
FIG. 5 is an exploded perspective view of a kit to treat erectile dysfunction according to another embodiment of the present invention.

Illustrated in FIG. 5 is another example of a kit to treat erectile dysfunction. The kit 75, for example, preferably includes a pressure pump 79, an outer vacuum chamber 59 and at least one inner vacuum chamber 65 positioned in a container 77. The inner vacuum chamber 65 is adapted to be inserted into the outer vacuum chamber 59. Each of the outer vacuum chamber 59 and the inner vacuum chamber 65 preferably has a proximal longitudinal end adapted to receive a patient's penis and a distal longitudinal end adapted to be positioned in fluid communication with the pressure pump 79. Depending on the timing during a course of treatment and condition of the penis, the outer vacuum chamber 59 may be connected to and in fluid communication with the pressure pump 57 without the inner vacuum chamber 65 positioned therein. Since the outer vacuum chamber 59 preferably has a different inner circumference than the inner vacuum chamber 65, patients having penises of different size and erectile dysfunction of varying degrees of severity may receive similar comfort and performance by using the vacuum chamber best suited to the patient's needs during operation of the pressure pump. The outer vacuum chamber 59 and inner vacuum chamber 65 also accommodate changes in the same patient over time. For example, a patient who has not had an erection in a long time will have less blood pulled into the penis. With vacuum treatment over time, the tissue inside the penis will hold more blood, resulting in more engorgement and a need for a vacuum chamber with a larger inner circumference.

The kit 75 further preferably includes an assortment of 15 penile tension devices 27-51' differing in inner circumference, material composition, tension type, and grip design. The assortment of penile tension devices may of course include more or less than 15 penile tension devices, and those devices may differ from one another by characteristics not described herein or not including some or all of the characteristics listed above, the assortment of penile tension devices of kit 75 serving only as an example. An assortment of penile tension devices is included so that different patients having penises of different size and erectile dysfunction of varying degrees of severity may receive similar comfort and performance by using the penile tension device best suited to the patient's needs. The assortment of penile tension devices 27-51' also accommodates changes in the same patient over time. For example, with treatment over time, a patient may require less tension from the penile tension device in order to maintain an erection, or vise versa. The preferred characteristics of penile tension devices 27-51' have been describe in relation to FIG. 1 and are summarized in FIG. 2.

The kit 75 to treat erectile dysfunction optionally may include additional components. For example, a loading cone for assisting in loading a penile tension device on a proximal longitudinal end of a vacuum chamber, cylinder sizing inserts for enhancing an airtight seal between a proximal longitudinal end of a vacuum chamber and the body of a user, a tube of lubricant, an instructional DVD, and an instruction manual could be included.

The difference between kit 54 illustrated in FIG. 3 and kit 75 illustrated in FIG. 5 is that the pressure pump 57 in kit 54 is a battery-driven pump, whereas the pressure pump 79 in kit 75 is a manual pump. For the battery-driven pump 57, one operates the pump by simply touching a button. Soma Blue Touch®II vacuum system, available from Augusta Medical Systems of Augusta, Ga., uses such a battery-driven pump. While for the manual pump 79, one operates the pump by pulling a handle attached to the pump body towards the pump using just one finger. Soma Blue Response®II, available from Augusta Medical Systems of Augusta, Ga., provides such an example.

The present invention also advantageously provides embodiments of systems to treat erectile dysfunction. An embodiment of a system includes a pressure pump, an elongated vacuum chamber selected from a plurality of elongated vacuum chambers positioned in a kit, and a penile tension device selected from a plurality of penile tension devices positioned in a kit. The vacuum chamber is positioned in fluid communication with the pressure pump at a distal longitudinal end thereof. A proximal longitudinal end of the vacuum chamber is adapted to receive a patient's penis. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. A first one of the plurality of penile tension devices preferably differs from a second one of the plurality of penile tension devices. The kit most preferably includes an assortment of penile tension devices differing in inner circumference, material composition, tension type, and grip design so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices.

Figure 6:
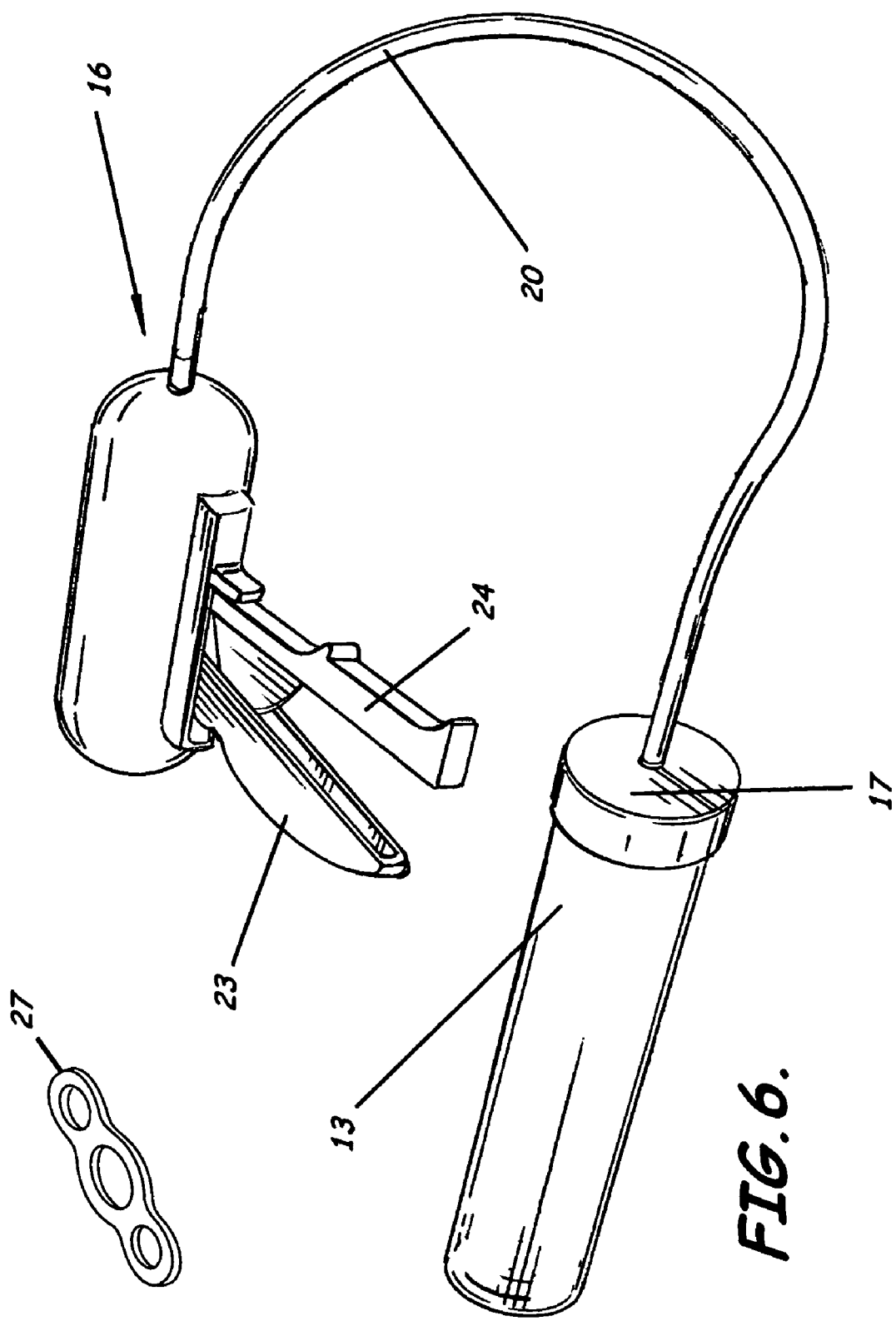
FIG. 6 is a perspective view of a system to treat erectile dysfunction according to an embodiment of the present invention.

As specifically illustrated in FIG. 6, for example, a system to treat erectile dysfunction preferably includes an elongated vacuum chamber 13, a pressure pump 16, fluid communication means 17 connected to the vacuum chamber 13 for establishing fluid communication between the chamber 13 and the pump 16, a flexible tube 20 connected to the fluid communication means 17 and the pressure pump 16, and a penile tension device 27. One operates the pressure pump 16 by pulling the actuation arm 24 toward the handle 23.

In this system, the vacuum chamber 13 is adapted to receive a patient's extremity at a proximal longitudinal end of the chamber. Depending on the timing during a course of a treatment and condition of the penis, vacuum chambers having different inner circumferences (e.g., chamber 14 or chamber 15 in FIG. 1) than the vacuum chamber 13 can be selected in place of chamber 13. Therefore, patients having penises of different size and erectile dysfunction of varying degrees of severity may receive similar comfort and performance by using the vacuum chamber best suited to the patient's needs during operation of the pressure pump. The three vacuum chamber 13, 14, and 15 also accommodate changes in the same patient over time. For example, a patient who has not had an erection in a long time will have less blood pulled into the penis. With vacuum treatment over time, the tissue inside the penis will hold more blood, resulting in more engorgement and a need for a larger vacuum chamber.

Penile tension device 27 is selected from a plurality of penile tension devices positioned in a kit, and differs from the other penile tension devices in the kit by, for example, inner circumference, material composition, tension type, or grip design. The kit preferably includes an assortment of 15 penile tension devices 27-51' as illustrated in FIGS. 1 and 2, any of which could be selected for use in the system. The assortment of penile tension devices may of course include more or less than 15 penile tension devices, and those devices may differ from one another by characteristics not described herein or not including some or all of the characteristics listed above, the assortment of penile tension devices of the kit serving only as an example. An assortment of penile tension devices is included so that different patients having penises of different size and erectile dysfunction of varying degrees of severity may receive similar comfort and performance by using the penile tension device best suited to the patient's needs. The assortment of penile tension devices 27-51' also accommodates changes in the same patient over time. For example, with treatment over time, a patient may require less tension from the penile tension device in order to maintain an erection, or vise versa.

Illustrated in FIGS. 7 and 8 are another example of a system to treat erectile dysfunction. This system preferably includes an outer vacuum chamber 59 and at least one inner vacuum chamber 65 adapted to be inserted into the outer vacuum chamber 59. Each of the outer chamber 59 and the inner chamber 65 preferably has a proximal longitudinal end adapted to receive a patient's penis and a distal longitudinal end adapted to be positioned in fluid communication with a pressure pump 57. A penile tension device 33 (FIG. 7) or 39 (FIG. 8) preferably also is included.

Depending on the timing during a course of treatment and condition of the penis, the outer vacuum chamber 59 may be connected to and in fluid communication with the pressure pump 57 without the inner vacuum chamber 65 positioned therein as illustrated in FIG. 7. Since the outer vacuum chamber 59 (FIG. 7) preferably has a different inner circumference than the inner vacuum chamber 65 (FIG. 8), patients having penises of different size and erectile dysfunction of varying degrees of severity may receive similar comfort and performance by using the vacuum chamber best suited to the patient's needs during operation of the pressure pump. The outer vacuum chamber 59 and inner vacuum chamber 65 also accommodate changes in the same patient over time. For example, a patient who has not had an erection in a long time will have less blood pulled into the penis. With vacuum treatment over time, the tissue inside the penis will hold more blood, resulting in more engorgement and a need for a vacuum chamber with a larger inner circumference.

Penile tension device 33 (FIG. 7) or 39 (FIG. 8) is selected from a plurality of penile tension devices positioned in a kit, and differs from the other penile tension devices in the kit by, for example, inner circumference, material composition, tension type, or grip design. An embodiment of a kit includes an assortment of penile tension devices 27-51' as illustrated in FIGS. 2 and 3, any of which could be selected for use in the systems of FIGS. 7 and 8. The assortment of penile tension devices may of course include more or less than 15 penile tension devices, and those devices may differ from one another by characteristics not described herein or not including some or all of the characteristics listed above, the assortment of penile tension devices of the kit serving only as an example. An assortment of penile tension devices is included so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices. The assortment of penile tension devices 27-51' also accommodates changes in the same patient over time. For example, with treatment over time, a patient may require less tension from the penile tension device in order to maintain an erection, or vise versa.

Illustrated in FIGS. 9 and 10 are yet another example of a system to treat erectile dysfunction. This system preferably includes an outer vacuum chamber 59 and at least one inner vacuum chamber 65 adapted to be inserted into the outer vacuum chamber 59. Each of the outer chamber 59 and the inner chamber 65 preferably has a proximal longitudinal end adapted to receive a patient's penis and a distal longitudinal end adapted to be positioned in fluid communication with a pressure pump 57. A penile tension device 45 (FIG. 9) or 51 (FIG. 8) preferably also is included.

Depending on the timing during a course of treatment and condition of the penis, the outer vacuum chamber 59 may be connected to and in fluid communication with the pressure pump 79 without the inner vacuum chamber 65 positioned therein as illustrated in FIG. 9. Since the outer vacuum chamber 59 (FIG. 9) preferably has a different inner circumference than the inner vacuum chamber 65 (FIG. 10), patients having penises of different size and erectile dysfunction of varying degrees of severity may receive similar comfort and performance by using the vacuum chamber best suited to the patient's needs during operation of the pressure pump. The outer vacuum chamber 59 and inner vacuum chamber 65 also accommodate changes in the same patient over time. For example, a patient who has not had an erection in a long time will have less blood pulled into the penis. With vacuum treatment over time, the tissue inside the penis will hold more blood, resulting in more engorgement and a need for a vacuum chamber with a larger inner circumference.

Penile tension device 45 (FIG. 9) or 51 (FIG. 10) is selected from a plurality of penile tension devices positioned in a kit, and differs from the other penile tension devices in the kit by, for example, inner circumference, material composition, tension type, or grip design. The kit preferably includes an assortment of penile tension devices 27-51' as illustrated in FIGS. 2 and 5, any of which could be selected for use in the systems of FIGS. 9 and 10. The assortment of penile tension devices may of course include more or less than 15 penile tension devices, and those devices may differ from one another by characteristics not described herein or not including some or all of the characteristics listed above, the assortment of penile tension devices of the kit serving only as an example. An assortment of penile tension devices is included so that different patients having penises of different size and erectile dysfunction of varying degrees of severity may receive similar comfort and performance by using the penile tension device best suited to the patient's needs. This assortment of the plurality of tension devices preferably includes a range to cover the varying degrees of severity and yet receive similar comfort. For example, an embodiment as illustrated and described includes 15 penile tension devices. The assortment of penile tension devices 27-51' also accommodates changes in the same patient over time. For example, with treatment over time, a patient may require less tension from the penile tension device in order to maintain an erection, or vise versa.

The difference between the system illustrated in FIGS. 7-8 and the system illustrated in FIGS. 9-10 is that the pressure pump 57 is a battery-driven pump, whereas the pressure pump 79 is a manual pump. For the battery-driven pump 57, one operates the pump by simply touching a button. Soma Blue Touch®II vacuum system, available from Augusta Medical Systems of Augusta, Ga., uses such a battery-driven pump. While for the manual pump 79, one operates the pump by pulling a handle attached to the pump body towards the pump using just one finger. Soma Blue Response®II, available from Augusta Medical Systems of Augusta, Ga., provides such an example.

Additionally, the present invention advantageously includes methods of treating erectile dysfunction. A method, for example, preferably includes the steps of examining a patient in order to determine at least the length and girth of the patient's penis and the severity of the patient's erectile dysfunction, selecting an elongated vacuum chamber from a plurality of vacuum chambers positioned in a kit based upon the examination, and selecting a penile tension device from a plurality of penile tension devices positioned in the kit based upon the examination. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. A first one of the plurality of penile tension devices preferably differs from a second one of the plurality of penile tension devices. The kit most preferably includes an assortment of 15 penile tension devices differing in inner circumference, material composition, tension type, and grip design so that different patients having penises of different size and erectile dysfunction of varying degrees of severity may receive similar comfort and performance by using the penile tension device best suited to the patient's needs. One embodiment of the method may further comprise the steps of placing the patient's penis inside the selected vacuum chamber, pumping air out of the chamber to create a pressure therewithin, maintaining the pressure within the chamber until an erection of a desired magnitude is achieved, removing the vacuum chamber, and stretching the selected penile tension device over a distal end of the patient's penis and toward a proximal portion of the penis. Another embodiment of the method may further comprise the steps of stretching the selected penile tension device over the proximal longitudinal end of the selected vacuum chamber, placing the patient's penis inside the selected vacuum chamber, pumping air out of the chamber to create a pressure therewithin, maintaining the pressure within the chamber until an erection of a desired magnitude is achieved, repositioning the selected penile tension device off the proximal longitudinal end of the chamber and onto a proximal portion of the penis of the user, and removing the chamber.

More specifically, a method of treating erectile dysfunction includes the step of examining a patient in order to determine at least the length and girth of the patient's penis and the severity of the patient's erectile dysfunction. The examining step may be performed by a health care professional, such as a physician or a vacuum therapy technician. Alternatively, the examining step could be performed by the patient himself with the assistance of, for example, a measuring device, sizing template, instruction manual, or Internet application. A next step in the method of treating erectile dysfunction includes the step of selecting an elongated vacuum chamber from a plurality of elongated vacuum chambers positioned in a kit based upon the examination, each chamber having a proximal longitudinal end adapted to receive the patient's penis and a distal longitudinal end adapted to be positioned in fluid communication with a pressure pump. A first one of the plurality of vacuum chambers preferably has a different inner circumference than a second one of the plurality of vacuum chambers so that different patients having penises of different size and erectile dysfunction of varying degrees of severity may receive similar comfort and performance by using the vacuum chamber best suited to the patient's needs during operation of the pressure pump. The kit most preferably includes three vacuum chambers, or an outer vacuum chamber and at least one inner vacuum chamber, each chamber having a different inner circumference than each other chamber. A further step in the method of treating erectile dysfunction includes the step of selecting a penile tension device from a plurality of penile tension devices positioned in the kit based upon the examination. A first one of the plurality of penile tension devices preferably differs from a second one of the plurality of penile tension devices. The kit most preferably includes an assortment of 15 penile tension devices differing in inner circumference, material composition, tension type, and grip design so that different patients having penises of different size and erectile dysfunction of varying degrees of severity may receive similar comfort and performance by using the penile tension device best suited to the patient's needs. The selecting steps may be performed by a health care professional, such as a physician or a vacuum therapy technician. Alternatively, the selecting steps could be performed by a computer program stored in a tangible medium, as understood by those skilled in the art, responsive to and used by the patient. Most preferably, the computer program comprises an Internet application assessable to the patient or physician over the Internet; however, the patient alternatively might receive a copy of the computer program for use on his own computer or access the program telephonically. The computer program preferably would lead the patient through a proper examination and then use examination data collected from the patient to select the proper vacuum chamber and penile tension device for the patient.

Additionally, kits, systems, and methods as may be included by distributing and sizing through an interactive Internet website or other electronic communication as understood by those skilled in the art. For example, a potential user can visit a preselected website to view and study information about a kit or system. The potential user can then follow preselected steps or instructions as to how sizing of a vacuum chamber or penile tensioning device is determined for the particular user, thereby allowing the user more private in home, or other locale, selection. Based on this information, the user can either be directed to a physician for confirmation of sizing and comfort, order a kit having the plurality of sizes of penile tension devices, order a kit having a plurality of vacuum chambers, order one or more preselected vacuum chamber and one or more penile tensioning devices, or one or more combinations as described.

As a condition of the patient's penis changes over a course of treatment and the patient's severity of erectile dysfunction changes, the examining and selecting steps may be repeated to ensure that the patient continues to use the correct vacuum chamber and penile tension device for his current condition. For example, examination of the condition of the patient and selection of a vacuum chamber and penile tension device could be conducted before or during a first usage of a vacuum treatment system by the patient. Thereafter, examination and selection might occur each month, or on various predetermined dates.

Figure 11:
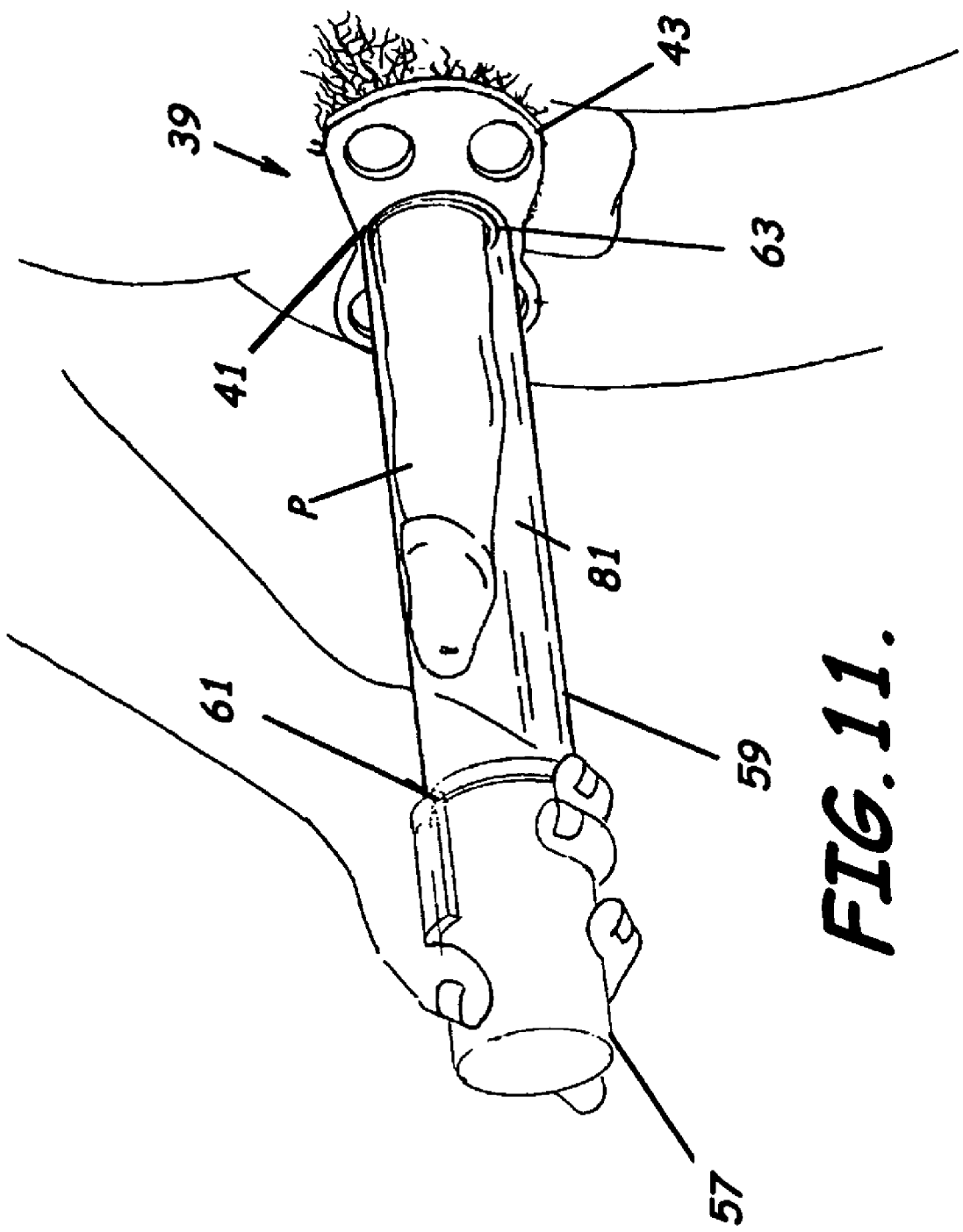
FIG. 11 is an environmental perspective view of a user using a system to treat penile erectile dysfunction according to an embodiment of the present invention.

FIG. 11 illustrates a method of treating erectile dysfunction using a vacuum treatment system after selection of a proper vacuum chamber 59 and penile tension device 39. The vacuum treatment system illustrated in FIG. 11 is similar to that illustrated in FIG. 7, except that penile tension device 39 has been selected rather than penile tension device 33. In the method, vacuum pump 57 is placed in fluid communication with vacuum chamber 59 at distal longitudinal end 61 thereof. The method includes stretching the selected penile tension device 39 over the proximal longitudinal end 63 of the selected vacuum chamber 59. Penile tension device 39 has center opening 41 and grip 43. The method next includes placing the patient's penis P inside of the selected vacuum chamber 59 from the proximal longitudinal end 63 thereof, the proximal longitudinal end 63 being pressed against the patient's body to ensure an airtight seal. The method also includes pumping air out of selected vacuum chamber 59 from the distal longitudinal end 61 thereof to create a pressure in space 81 of vacuum chamber 59 to create an erect penis. The method additionally includes maintaining the pressure within vacuum chamber 59 until an erection of a desire magnitude is achieved in penis P. The method further includes repositioning the penile tension device 39 off proximal longitudinal end 63 of vacuum chamber 59 and onto a proximal portion of penis P. Finally, the method provides for removing vacuum chamber 59.

Figure 12:
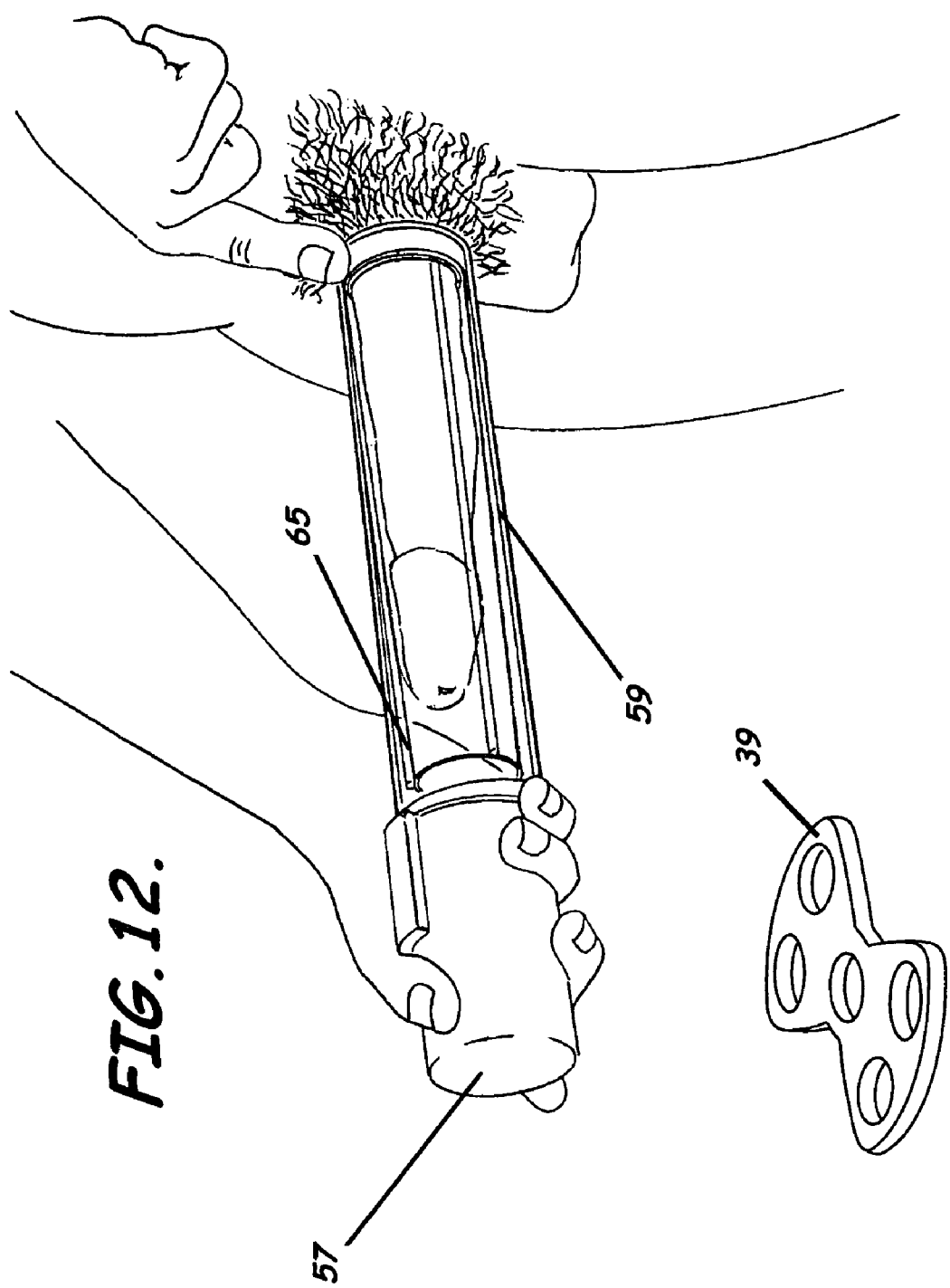
FIG. 12 is an environmental perspective view illustrating placement of a penis of a user in a system to treat penile erectile dysfunction according to an embodiment of the present invention.
Figure 13:
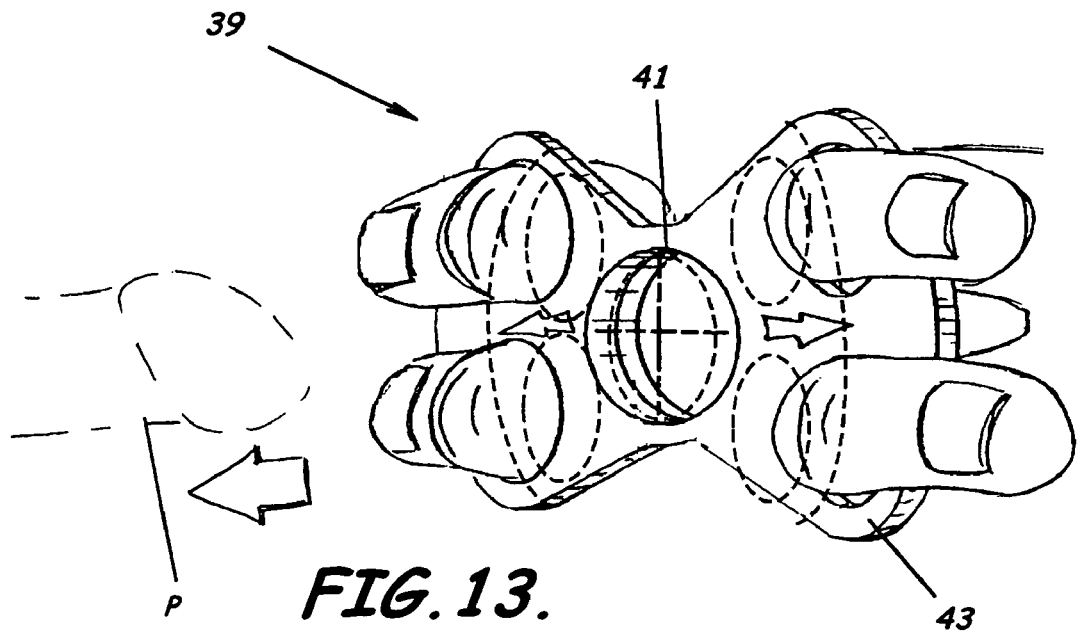
FIG. 13 is an environmental perspective view of a penile tension device according to an embodiment of the present invention.
Figure 14:
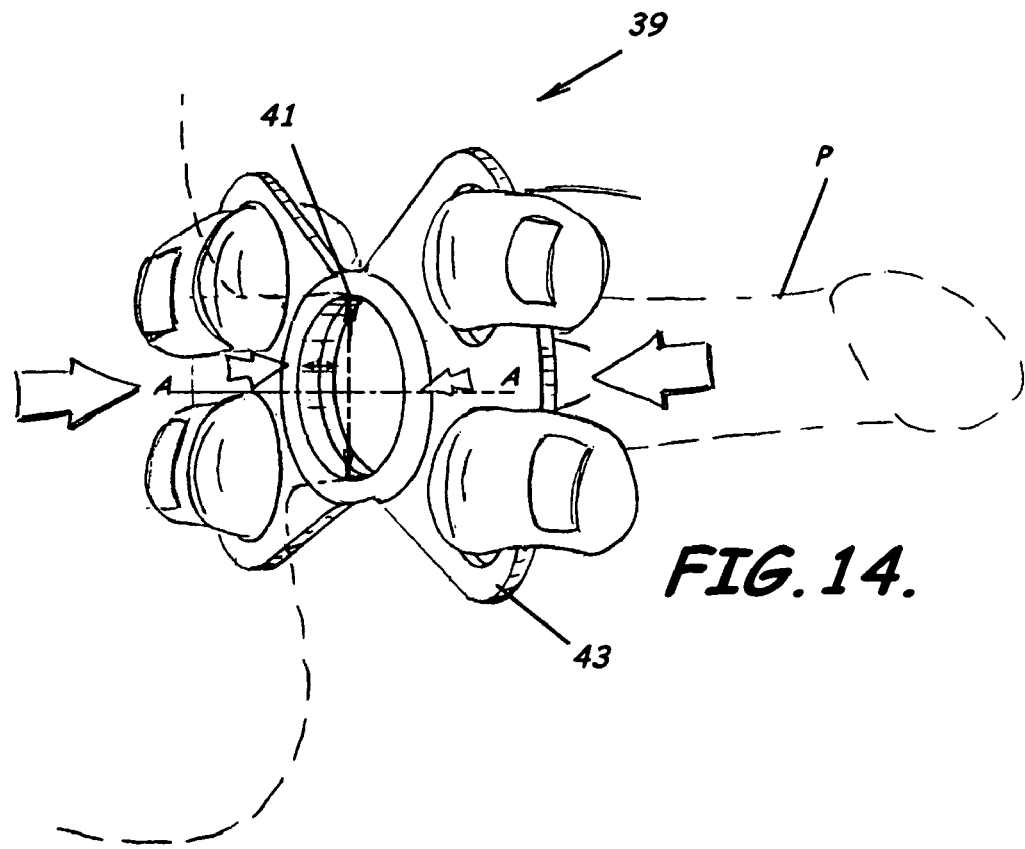
FIG. 14 is an environmental perspective view of the penile tension device of FIG. 13 positioned at the base or proximal end portion of a penis according to an embodiment of the present invention.

FIG. 12 illustrates a further method of treating erectile dysfunction using a vacuum treatment system. The method of FIG. 12 is similar to the method of FIG. 11. In this method, inner vacuum chamber 65 has been selected and positioned within vacuum chamber 59, both of which are placed in fluid communication with vacuum pump 57. The method includes placing the patient's penis inside vacuum chambers 59 and 65, pumping air out of the vacuum chambers, maintaining the pressure within the vacuum chambers until an erection of a desired magnitude is achieved, and removing the vacuum chamber. Next, as best illustrated in FIGS. 13 and 14, the method includes stretching the selected penile tension device, in this case penile tension device 39, over a distal end of the patient's penis P and toward a proximal portion of the penis P. The patient uses his fingers in cooperation with grip 43 to stretch center opening 41 over the distal end of penis P. The penile tension device, here penile tension device 39, is then moved toward the proximal end or base of penis P, where the patient disengages his fingers from grip 43, causing a pressure at the base of penis P for maintaining the erection.

In the drawings and specification, there have been disclosed embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That claimed is:

1. A kit comprising:
   (a) a container;
   (b) a pressure pump positioned in the container;
   (c) a plurality of elongated vacuum chambers positioned in the container, each chamber having a proximal longitudinal end adapted to receive a patient's penis and a distal longitudinal end adapted to be positioned in fluid communication with the pressure pump, a first one of the plurality of elongated vacuum chambers having a different inner circumference than a second one of the plurality of elongated vacuum chambers; and
   (d) a plurality of penile tension devices positioned in the container, a first one of the plurality of penile tension devices differing from a second one of the plurality of penile tension devices.

2. The kit of claim 1, wherein the first penile tension device differs from the second penile tension device by one or more of inner circumference, material composition, tension level, and grip design.

3. The kit of claim 1, wherein the plurality of penile tension devices comprises an assortment of penile tension devices differing in inner circumference, material composition, tension level, and grip design.

4. The kit of claim 3, wherein the assortment of penile tension devices comprises 15 penile tension devices.

5. The kit of claim 3, wherein the plurality of penile tension devices have a range of inner circumferences in the range of ¼th inch to one inch and a tension level from low to high.

6. The kit of claim 1, wherein the plurality of elongated vacuum chambers comprises three vacuum chambers, each of the three vacuum chambers having a different inner circumference than each of the other ones of the three vacuum chambers.

7. The kit of claim 1, wherein the first vacuum chamber comprises an outer vacuum chamber and the second vacuum chamber comprises at least one inner vacuum chamber adapted to be inserted into the outer vacuum chamber, the outer vacuum chamber having a proximal longitudinal end adapted to receive the patient's penis and a distal longitudinal end adapted to be positioned in fluid communication with the pressure pump, the at least one inner vacuum chamber also having a proximal longitudinal end adapted to receive the patient's penis and a distal longitudinal end adapted to be positioned in fluid communication with the pressure pump, the outer vacuum chamber having a different inner circumference than the at least one inner vacuum chamber.

8. The kit of claim 7, wherein the outer vacuum chamber includes a user interface adapted to be positioned on an inner surface thereof to interface with the at least one inner vacuum chamber.

9. The kit of claim 8, wherein the outer vacuum chamber user interface comprises an inner flange positioned adjacent the proximal longitudinal end of the outer vacuum chamber and connected to and extending inwardly from an inner surface of the outer vacuum chamber to thereby define an inner step formed therein from the proximal longitudinal end thereof, and wherein the at least one inner vacuum chamber comprises a plurality of stop members extending outwardly from an outer surface of the at least one inner vacuum chamber to interface with and contact the inner step of the outer vacuum chamber to thereby limit the inward movement of the at least one inner vacuum chamber when positioned within the outer vacuum chamber.

10. The kit of claim 9, wherein the at least one inner vacuum chamber further comprises a plurality of spaced-apart ribs connected to and extending outwardly from the outer surface thereof to provide separation between the outer surface of the at least one inner vacuum chamber and the inner surface of the outer vacuum chamber so that an interstitial space is formed there between when the at least one inner vacuum chamber is positioned within the outer vacuum chamber.

11. A system for treating erectile dysfunction comprising:
   (a) a pressure pump;
   (b) an elongated vacuum chamber positioned in fluid communication with the pressure pump and selected from a plurality of elongated vacuum chambers positioned in a kit, each chamber having a proximal longitudinal end adapted to receive a patient's penis and a distal longitudinal end adapted to be positioned in fluid communication with the pressure pump, a first one of the plurality of elongated vacuum chambers having a different inner circumference than a second one of the plurality of elongated vacuum chambers; and
   (c) a penile tension device selected from a plurality of penile tension devices positioned in the kit, a first one of the plurality of penile tension devices differing from a second one of the plurality of penile tension devices.

12. The system of claim 11, wherein the first penile tension device differs from the second penile tension device by one or more of inner circumference, material composition, tension level, and grip design.

13. The system of claim 11, wherein the plurality of penile tension devices comprises an assortment of penile tension devices differing in inner circumference, material composition, tension level, and grip design.

14. The system of claim 13, wherein the assortment of penile tension devices comprises 15 penile tension devices.

15. The kit of claim 13, wherein the plurality of penile tension devices have a range of inner circumferences in the range of ¼th inch to one inch and a tension level from low to high.

16. The system of claim 11, wherein the plurality of elongated vacuum chambers comprises three vacuum chambers, each of the three vacuum chambers having a different inner circumference than each of the other ones of the three vacuum chambers.

17. The system of claim 11, wherein the first vacuum chamber comprises an outer vacuum chamber and the second vacuum chamber comprises at least one inner vacuum chamber adapted to be inserted into the outer vacuum chamber, the outer vacuum chamber having a proximal longitudinal end adapted to receive the patient's penis and a distal longitudinal end adapted to be positioned in fluid communication with the pressure pump, the at least one inner vacuum chamber also having a proximal longitudinal end adapted to receive the patient's penis and a distal longitudinal end adapted to be positioned in fluid communication with the pressure pump, the outer vacuum chamber having a different inner circumference than the at least one inner vacuum chamber.

18. The system of claim 17, wherein the outer vacuum chamber includes a user interface adapted to be positioned on an inner surface thereof to interface with the at least one inner vacuum chamber.

19. The system of claim 18, wherein the outer vacuum chamber user interface comprises an inner flange positioned adjacent the proximal longitudinal end of the outer vacuum chamber and connected to and extending inwardly from an inner surface of the outer vacuum chamber to thereby define an inner step formed therein from the proximal longitudinal end thereof, and wherein the at least one inner vacuum chamber comprises a plurality of stop members extending outwardly from an outer surface of the at least one inner vacuum chamber to interface with and contact the inner step of the outer vacuum chamber to thereby limit the inward movement of the at least one inner vacuum chamber when positioned within the outer vacuum chamber.

20. The system of claim 19, wherein the at least one inner vacuum chamber further comprises a plurality of spaced-apart ribs connected to and extending outwardly from the outer surface thereof to provide separation between the outer surface of the at least one inner vacuum chamber and the inner surface of the outer vacuum chamber so that an interstitial space is formed there between when the at least one inner vacuum chamber is positioned within the outer vacuum chamber.

21. The system of claim 11, wherein the elongated vacuum chamber is selected from the plurality of elongated vacuum chambers positioned in the kit by a healthcare professional at a predetermined time and the penile tension device is selected from the plurality of penile tension devices positioned in the kit by the healthcare professional at the predetermined time.

22. The system of claim 21, wherein the healthcare professional bases the selection of vacuum chamber and penile tension device on a plurality of factors including the length and girth of the patient's penis, and the severity of the patient's erectile dysfunction.

23. The system of claim 11, wherein the elongated vacuum chamber is selected from the plurality of elongated vacuum chambers positioned in the kit by a software program at a predetermined time and the penile tension device is selected from the plurality of penile tension devices positioned in the kit by the software program at the predetermined time.

24. The system of claim 23, wherein the software program comprises an Internet application, and the Internet application bases the selection of vacuum chamber and penile tension device on a plurality of factors input by the patient including the length and girth of the patient's penis, and the severity of the patient's erectile dysfunction.

25. A method of treating erectile dysfunction comprising the steps of:
   (a) examining a patient in order to determine at least the length and girth of the patient's penis and the severity of the patient's erectile dysfunction;
   (b) selecting an elongated vacuum chamber from a plurality of elongated vacuum chambers positioned in a kit based upon the examination, each chamber having a proximal longitudinal end adapted to receive the patient's penis and a distal longitudinal end adapted to be positioned in fluid communication with a pressure pump, a first one of the plurality of elongated vacuum chambers having a different inner circumference than a second one of the plurality of elongated vacuum chambers; and
   (c) selecting a penile tension device from a plurality of penile tension devices positioned in the kit based upon the examination, a first one of the plurality of penile tension devices differing from a second one of the plurality of penile tension devices.

26. The method of claim 25, wherein a health care professional performs the examining and selecting steps.

27. The method of claim 25, wherein the patient performs the examining step and a computer program stored on a tangible medium and responsive to the patient assists the patient in performing the selecting steps.

28. The method of claim 27, wherein the computer program comprises an Internet application.

29. The method of claim 25, wherein performance of the examining and selecting steps occur at a preselected time.

30. The method of claim 25, further comprising the steps of:
   placing the patient's penis inside of the selected vacuum chamber from the proximal longitudinal end thereof, the proximal longitudinal end being pressed against the patient's body to ensure an airtight seal;
   pumping air out of the selected vacuum chamber from the distal longitudinal end thereof to create a pressure there within;
   maintaining the pressure within the selected vacuum chamber until an erection of a desired magnitude is achieved;
   removing the selected vacuum chamber;
   stretching the selected penile tension device over a distal end of the patient's penis and toward a proximal portion of the penis.

31. The method of claim 30, further comprising the steps of
   stretching the selected penile tension device over the proximal longitudinal end of the selected vacuum chamber;
   placing the patient's penis inside of the selected vacuum chamber from the proximal longitudinal end thereof, the proximal longitudinal end being pressed against the patient's body to ensure an airtight seal;
   pumping air out of the selected vacuum chamber from the distal longitudinal end thereof to create a pressure there within;
   maintaining the pressure within the selected vacuum chamber until an erection of a desired magnitude is achieved;
   repositioning the selected penile tension device off the proximal longitudinal end of the selected vacuum chamber and onto a proximal portion of the penis; and
   removing the selected vacuum chamber.

* * * * *